US010163527B2

(12) United States Patent
Eckman et al.

(10) Patent No.: US 10,163,527 B2
(45) Date of Patent: Dec. 25, 2018

(54) USER INTERFACE DISPLAYING A TEMPORAL RELATIONSHIP BETWEEN A HEALTH EVENT INDICATOR AND MONITORED HEALTH CONDITIONS

(71) Applicant: Preventice Technologies, Inc., Rochester, MN (US)

(72) Inventors: George F. Eckman, Rochester, MN (US); Mark L. Holm, Rochester, MN (US); Richard M. Smith, Oronoco, MN (US)

(73) Assignee: Preventice Technologies, Inc., Rochester, MN (US)

( * ) Notice: Subject to any disclaimer, the term of this patent is extended or adjusted under 35 U.S.C. 154(b) by 20 days.

(21) Appl. No.: 14/973,553

(22) Filed: Dec. 17, 2015

(65) Prior Publication Data

US 2016/0321430 A1    Nov. 3, 2016

Related U.S. Application Data

(60) Provisional application No. 62/153,989, filed on Apr. 28, 2015.

(51) Int. Cl.
*G06F 19/00* (2018.01)
*G06T 11/20* (2006.01)
(Continued)

(52) U.S. Cl.
CPC .......... *G16H 15/00* (2018.01); *G06F 19/3418* (2013.01); *G06T 11/206* (2013.01); *G16H 40/63* (2018.01); *G16H 50/20* (2018.01)

(58) Field of Classification Search
CPC ............. G06F 19/3406; G06F 19/3487; G06F 19/322; G06F 19/345; G06F 19/3418;
(Continued)

(56) References Cited

U.S. PATENT DOCUMENTS 9,472,002 B1 * 10/2016 Wong ..................... G06F 9/00
2005/0113706 A1 * 5/2005 Prystowsky ......... A61B 5/0006
600/518
(Continued)

FOREIGN PATENT DOCUMENTS

WO    2014047171 A1    3/2014

OTHER PUBLICATIONS

Google, Controls and Dashboards, 2010, URL: https://developers.google.com/chart/interactive/docs/gallery/controls#chartrangefilter, pp. 1.*

(Continued)

*Primary Examiner* — Said Broome
*Assistant Examiner* — Phuc N Doan
(74) *Attorney, Agent, or Firm* — Patterson + Sheridan, LLP

(57) ABSTRACT

Techniques for generating a user interface for monitoring biometric data. Embodiments generate a first portion of the user interface by plotting values of a first biometric parameter on a first graph structure with respect to a first interval of time and generate a second portion of the user interface by plotting values of a second biometric parameter on a second graph structure with respect to a second interval of time that overlaps with only a portion of the first interval of time. Upon receiving a user selection specifying a first position within the first graph structure, embodiments determine a third interval of time that is centered at a moment in time corresponding to the specified first position and update the second graph structure by plotting a third plurality of values of the second biometric parameter on the second graph structure, with respect to the third interval of time.

20 Claims, 11 Drawing Sheets

(51) Int. Cl.
*G16H 50/20* (2018.01)
*G16H 15/00* (2018.01)
*G16H 40/63* (2018.01)

(58) Field of Classification Search
CPC ............... G06F 3/04845; G06F 3/0481; G06F 3/04847; G06F 2203/04806; G06T 11/206; G01R 13/0218; G01R 1/025; G01R 23/16
See application file for complete search history.

(56) References Cited

U.S. PATENT DOCUMENTS

| | | | |
|---|---|---|---|
| 2007/0123788 A1* | 5/2007 | Gunderson | A61B 5/0006 600/510 |
| 2007/0203816 A1* | 8/2007 | Costache | G06Q 40/00 705/35 |
| 2008/0297513 A1* | 12/2008 | Greenhill | G06Q 99/00 345/440 |
| 2009/0006241 A1* | 1/2009 | Zhao | G06Q 40/04 705/37 |
| 2010/0333001 A1* | 12/2010 | Wild | G06F 3/04847 715/764 |
| 2011/0004110 A1* | 1/2011 | Shusterman | G06F 19/3443 600/509 |
| 2011/0074788 A1 | 3/2011 | Regan et al. | |
| 2011/0245698 A1* | 10/2011 | Wang | A61B 5/024 600/509 |
| 2013/0141466 A1* | 6/2013 | Earls | G01R 23/16 345/660 |
| 2013/0245463 A1* | 9/2013 | Stuebe | G06F 19/3487 600/483 |
| 2013/0271469 A1* | 10/2013 | Moore | G06T 11/206 345/440.1 |
| 2013/0271470 A1* | 10/2013 | Moore | G06F 19/322 345/440.1 |
| 2014/0088994 A1* | 3/2014 | Kroh | G06F 19/345 705/2 |
| 2014/0222446 A1* | 8/2014 | Ash | G06Q 50/22 705/2 |
| 2014/0258198 A1* | 9/2014 | Spivack | G06N 5/046 706/21 |
| 2014/0315170 A1* | 10/2014 | Ionescu | G06F 19/3456 434/236 |
| 2015/0012297 A1 | 1/2015 | Ash et al. | |
| 2015/0035772 A1* | 2/2015 | Asahara | B63B 49/00 345/173 |
| 2015/0073237 A1* | 3/2015 | Osorio | A61B 5/0245 600/301 |
| 2015/0248534 A1* | 9/2015 | Krzywicki | G06F 19/3406 715/771 |
| 2016/0135706 A1* | 5/2016 | Sullivan | A61B 5/0059 600/301 |
| 2016/0275661 A1* | 9/2016 | Goard | G06F 17/30 |

OTHER PUBLICATIONS

International Search Report and Written Opinion for PCT/US2016/029178 dated Jul. 19, 2016.

\* cited by examiner

USER INTERFACE DISPLAYING A TEMPORAL RELATIONSHIP BETWEEN A HEALTH EVENT INDICATOR AND MONITORED HEALTH CONDITIONS

CROSS-REFERENCE TO RELATED APPLICATIONS

This application claims benefit of U.S. provisional patent application Ser. No. 62/153,989, filed Apr. 28, 2015, which is herein incorporated by reference in its entirety.

TECHNICAL FIELD

The present disclosure relates to decision-support systems for patient healthcare, and in particular, to data display systems for patient health information.

BACKGROUND

Benefits of medical data display systems include rapid presentations and storage of data of monitored health conditions for a patient. At least some of this information may be generated by electronic sensors configured to detect at least one medical condition of a patient and produce an electronic signal based on that medical condition. The electronic signal may be collected over time in at least one standard metric used in the care of the patient may be determined for analysis by a medical care provider. Examples of a standard metric may include heart rates and electrocardiogram data. Data for the standard metric can be collected over extended timeframes, for example, in some cases twenty-four hours or more to monitor the health of the patient and to identify abnormalities which may occur with frequencies that may vary on a patient-to-patient basis. The abnormalities may be observable as changes in the standard metric occurring at occurrences that are predictable or still being understood. The abnormalities may be used by the medical care provider to provide long term care to the patient, predict future medical events, or to diagnose medical conditions of the patient.

As the amount of medical data in the form of electrical signals from the patient becomes more readily available and the time demands on the medical caregiver continue to increase, there is a need to more efficiently provide assistance to the care provider to provide convenient access to the at least one standard metric. In some cases, the at least one standard metric may conventionally be generated as an electrocardiogram hardcopy data printout and the caregiver must meticulously review the long hardcopy strip which may include twenty-four hours or more of data to determine abnormalities in a time consuming process. Further, in some cases the care provider often correlates that at least one standard metric to other data, for example, a second standard metric in the form of heat rates to monitor the health of the patient. Correlating multiple metrics can also be a time consuming endeavor and prone to errors as the large quantities of data are often difficult to analyze and compare particularly under the stressful environment of a care provider facility where medical care decisions may necessarily need to be made very quickly to ensure that the patient receives accurate and timely care. New approaches are needed to enable care providers to more easily recognize and understand the occurrence and identities of health events experienced by patients, so that care providers may be better informed to provide more effective treatments.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

To facilitate understanding, identical reference numerals have been used, where possible, to designate identical elements that are common to the figures. It is contemplated that elements disclosed in one embodiment may be beneficially utilized on other embodiments without specific recitation.

DESCRIPTION OF EXAMPLE EMBODIMENTS

Overview

Figure 1:
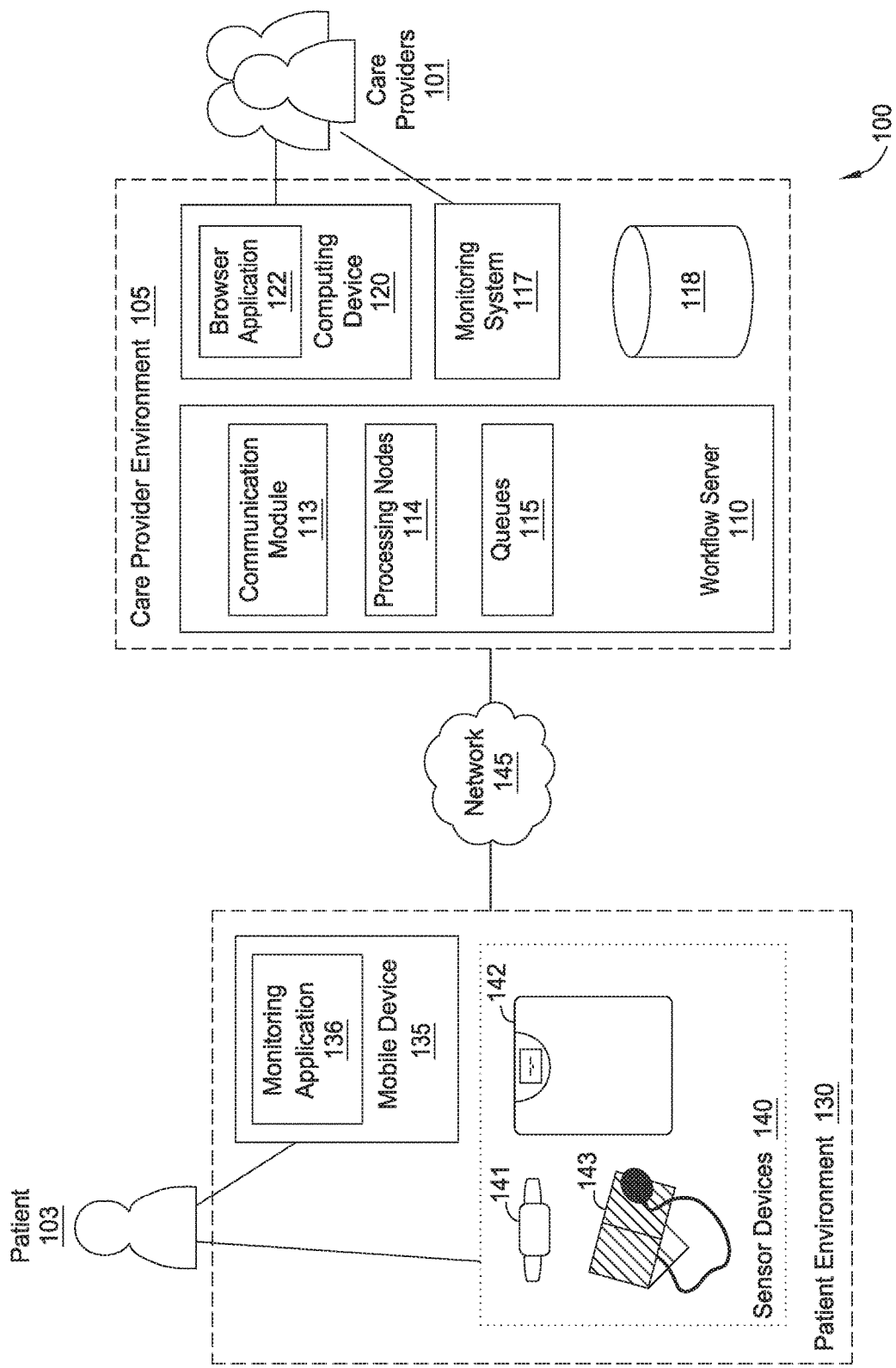
FIG. 1 illustrates an example computing environment, according to one embodiment.

A user interface displaying a temporal relationship between a health event indicator and monitored health conditions is disclosed. The user interface may be part of an electronic device including a computer monitor, processor, and computer-readable instructions. The processor is configured to follow the computer-readable instructions to receive an input signal based on at least one electronic signal from at least one sensor measuring a respective at least one medical condition of the patient. The computer monitor includes pixels and is configured to receive a display signal from the processor and present data graphs based on the display signal using the pixels readable by a caregiver. A first data graph includes heat rate information of the patient in the ordinate axis as a function of time along the abscissa axis. The first graph also includes at least one health event wherein each is represented as distinct icon aligned parallel to the abscissa axis and positioned according to a time the health event occurred. The processor is configured to provide navigational aids to the care provider, so the care provider can select a desired time within the first graph. Upon selecting the desired time, second and third graphs may respectively display first and second portions of electrocardiogram data associated with the desired time. By including the single icons representing the ECG events as part of the first graph, the care provider may more easily determine the desired time based on the occurrence, or non-occurrence, of the health events. In this manner, the care provider may save time and reduce errors as part of treatment of the patient by more efficiently and accurately determining relationships between biometric data and health events.

One embodiment provides a method for processing health events in a workflow. The method includes receiving a health event for a patient derived from monitoring biometric data generated by one or more sensor devices and identifying a type of the health event by classifying biometric data associated with the health event. The method includes processing the health event using a plurality of interconnected processing nodes based on the type of the health event and a priority assigned to the health event, where each processing node comprises respective sets of consumers and each set is assigned to process health events at a different priority level.

Additional embodiments provide a computer-readable medium and system for carrying out the aforementioned method.

Example Embodiments

Network aware devices provide a variety of opportunities for a care provider (e.g., a physician, nurse, technician, etc.) to improve patient care. An event manager can use the data provided by network aware devices or an "internet of things" (IoT) device to identify health events that range from identifying critical health care issues such as cardiac or respiratory emergencies to maintenance events where the network aware device fails, e.g., because a battery is low or a wire is disconnected. To process health related events, an event manager may process events using a collection of defined paths.

In one embodiment, a group of servers each host an event engine with a respective set of interconnected tasks and queues that form a workflow. The group of servers may include a load balancer which routes the biometric data measured by the IoT devices to one of the servers for processing. Because the biometric data is processed using different tasks, the event engines can process multiple health events simultaneously. Stated differently, the event engines process the health events using a series of operations in the workflow where each operation (or task) can process a respective health event in parallel.

In one embodiment, the event engines classify health events received from the at least one sensor devices which may be worn by the patient. For example, a device may have classified the health event as one type of event. However, the workflows in the event engines may process the biometric data associated with the event to confirm the initial classification or reclassify or reprioritize the health event as a different type of event. Alternatively, the sensor device may send biometric data to the servers which then use one or more thresholds or rules to identify health events which are then processed by the workflows in the event engines. The workflows determine actions to take when processing the health events such as notifying a care provider, suppressing or ignoring the event, or storing the event in a data repository. The event may also be displayed in a first graph of a user interface using a health event indicator for each occurrence of the health event with respect to time displayed on the abscissa axis. The first graph also depicts a monitored health condition with respect to the time displayed on the abscissa axis. In this manner, a temporal relationship between the health event indicator and the monitored health condition can be efficiently displayed.

In one embodiment, the workflows process the health events using a priority assigned to the health events. The priority may be assigned based on a severity of the event (e.g., an irregular heart beat versus a heart attack), the type of the health event, a characteristic of the patient whose biometric data generated the health event (e.g., the patient's age or past medical history), and the like. Processing nodes in the workflows may include multiple consumers (e.g., processing threads) for processing different priority health events. For example, a processing node may include ten consumers assigned to process high priority events, seven consumers assigned to process medium priority events, and five consumers assigned to process low priority events. By having more consumers assigned to high priority events, the latency for processing these events in the workflow may be reduced. In another example, the consumers assigned to process the higher priority health events may have more computer resources assigned to them—e.g., additional CPUs or memory—than consumers that process lower priority events in the node.

In this regard, FIG. 1 illustrates an example computing environment 100, according to one embodiment. As shown, the computing environment 100 may include a care provider environment 105 and a patient environment 130, each connected to one another via a network 145. The care provider environment 105 and the patient environment 130 allow a care provider 101 (e.g., a technician, nurse, physician, etc.) to monitor biometric data generated by the patient 103.

The care provider environment 105 includes a workflow server 110, a computing device 120, monitoring system 117 and data repository 118. Each of the workflow server 110, the computing device 120, and the monitoring system 117 may be a physical computing system that includes one or more computing devices 120A, 120B (FIG. 3) or a virtual computer instance (e.g., executing in a cloud computing platform). A care provider 101 may use the computing device 120 to access (e.g., via a browser application 122, a native application on device 120, etc.) a user interface (UI) hosted by the monitoring system 117.

Of note, although shown as a single entity, the data repository 118 can represent multiple, separate data stores (e.g., relational databases). Moreover, these data stores can span multiple computing nodes. To this end, the separate data stores could be made to function as a single data store (e.g., through data replication techniques and through the use of load balancers). As such, the data repository 118 is representative of any sort of data store on any number of computing systems, consistent with the functionality described herein.

Additionally, although not shown, the data repository 118 may store data from and/or service requests from various other entities, such as third party applications, partners and affiliates, electronic medical record systems, external monitoring devices and products, analytics engines, data consolidator applications and so on. More generally, it is contemplated that the data repository 118 and, more generally, other elements within the care provider environment 105, can interact with any number of different data originators and receipts, consistent with the functionality described herein. As such, the computing environment 100 is provided merely for illustrative purposes only and without limitation.

The workflow server 110 includes applications and data executed to identify and handle health events corresponding to the patient 103. As shown, workflow server 110 includes a communication module 113, processing nodes 114, and queues 115. In one embodiment, the processing nodes 114 are software code or applications that perform a predetermined task or action on received data (e.g., health events). The workflow server 110 evaluates data received from the patient environment 130 using a set of interconnected processing nodes 114 and the queues 115 which form a workflow. As the biometric data or health events are received from the patient environment 130, the workflow may classify (or reclassify) the data to identify a type of the health event—e.g., presentation or notification to patient/care provider, suppression, classification, aggregation, computation, prioritization/triage, and the like. For example, different types of data received from the patient environment 130 may trigger different types of health events—e.g., an irregular heartbeat may trigger a cardiac event, while a signal indicated an electrode has become detached triggers a maintenance event. In one embodiment, at least one sensor device 140 within the patient environment 130 or a monitoring application 136 installed as part of a mobile device 135 within the patient environment 130 may have performed an initial classification of the data or health events. Nonetheless, the workflow server 110 may evaluate the biometric data (or maintenance data) to confirm that this initial classification was correct.

Each type of health event may take a different path through the workflow. That is, different health events may traverse the processing nodes 114 and the queues 115 using different paths. For example, a cardiac event may be evaluated using different processing nodes 114 in the server 110 than a maintenance event. Furthermore, paths through the workflow for the same health event may differ based on a variety of factors such as the severity of the health event, age of the patient 103, other symptoms exhibited by the patient 103, medication taken by the patient 103, and the like. For example, a high priority cardiac event may skip one or more of the processing nodes 114 or the queues 115 and be immediately displayed to the care provider 101 using the monitoring system 117.

The communication module 113 permits the workflow server 110 to receive the data from the patient environment 130 and transmit data to the care providers 101. The communication module 113 may receive data from the at least one sensor device 140 which is used to identify a health event and a corresponding path through interconnected ones of the processing nodes 114 and the queues 115. The communication module 113 helps the care providers 101 complete the workflow by use of the monitoring system 117 and the computing device 120. Moreover, in addition to receiving the data from the patient environment 130, the communication module 113 may enable the workflow server 110 to transmit requests or instructions to the patient environment 130 such as asking the patient 103 if she has any symptoms or instructing the patient 103 to reattach a disconnected electrode (not shown) of the at least one sensor device 140.

In one embodiment, a path used by a health event to traverse the workflow server 110 may include processing nodes 114 that process the health event without user intervention as well as the processing nodes 114 that require input from the care providers 101. For example, one of the processing nodes 114 may filter or screen a health event to determine what queue to place the event, compare the event to one or more rules to determine an action to perform, or store the event. Alternatively, others of the processing nodes 114 may require the care provider 101 to perform an action or provide instructions. For example, the monitoring system 117 may generate a user interface (UI) for a health event which is then displayed to the care provider 101 by the browser application 122. Once the care provider 101 performs an action (e.g., confirms the classification of the event or agrees with an action suggested by the workflow server 110), the remaining operations of the workflow are performed—e.g., send a notification to the patient 103, log the event in the history of the patient 103, route the event to a different one of the care providers 101, reclassify the health event (if the care provider 101 indicated the initial classification was incorrect), or prioritize or triage the health event.

With continued reference to FIG. 1, the patient environment 130 includes the mobile device 135 and the at least one sensor device 140. The mobile device 135 includes the monitoring application 136 which permits communication between the at least one sensor device 140 and the care provider environment 105 via the network 145. The monitoring application 136 may configure the at least one sensor device 140 (e.g., IoT devices) to monitor biometric data of the one or more patient 103 as specified by a care plan. For example, the monitoring application 136 could configure logic on a heart rate monitoring device worn by the patient to monitor the patient's heart rate. In turn, the monitoring application 136 can send the heart rate data to the workflow server 110 which determines if a heath event is triggered, and if so, executes a workflow to process the event as described above. In another embodiment, the heart rate monitoring device, upon detecting that a threshold condition has been satisfied, could generate and transmit a health event to the mobile device 135, which in turn transmits the health event to the workflow server 110 for processing. However, in other embodiments, some of the tasks performed by the workflow server 110 may be performed by the mobile device 135. That is, the workflow may include tasks performed by the mobile device 135 or the at least one sensor device 140 as well as tasks performed by the workflow server 110.

In one embodiment, the monitoring application 136 receives environmental data from the at least one sensor device 140. Generally, the environmental data informs the monitoring application 136 of environmental conditions in an area proximate to the at least one sensor device 140 and the user—e.g., a room in which the user is located. For example, the at least one sensor device 140 may detect an air quality or pollen count for the patient 103 having a respiratory ailment. In another example, the at least one sensor device 140 may track the user's movements or actions in an environment such as how many times at night the patient 103 goes to the bathroom or if the patient 103 is tossing and turning at night. This environmental data can then be used by the monitoring application 136 by itself, or in combination with the biometric data, to trigger health events which are processed by the workflow server 110.

In one embodiment, the monitoring application 136 may use an output device (e.g., a display or audio system) on the mobile device 135 to provide information to the patient 103. For example, when executing a workflow, one of the processing nodes 114 may ask the patient 103 if she is experiencing any symptoms. To obtain feedback from the patient 103, the monitoring application 136 may display a user interface (UI) on the mobile device 135 which permits the patient 103 to list symptoms. Moreover, the monitoring application 136 may also display general information related to a care plan or the at least one sensor device 140 such as the patient's heart rate or weight, status of the at least one sensor device 140, etc. Additionally, the sensor devices 140 may also be configured with input/output devices which can be used to provide feedback to the patient. For example, a sensor device 142(1)-142(N) could be equipped with an input/output device (e.g., a display device, one or more speakers, light-emitting diodes, etc.) that can be used to provide feedback to the patient. In one embodiment, logic on the mobile device 135 is configured to control the output that is provided to the patient on the various input/output devices of the sensor devices 140.

In one embodiment, the at least one sensor device 140 interacts with the monitoring application 136 and assists the patient 103 in reporting patient vitals and other information to the care provider environment 105. As shown, the at least one sensor device 140 may include a body sensor 141, a weighing scale 142, and a blood pressure cuff 143. Each of the at least one sensor device 140 may capture different vitals of the patient 103. For example, when applied to a body of patient 103, the body sensor 141 captures biometric data (e.g., heart rate, ECG data, etc.) in real-time. In addition, each of the at least one sensor device 140 may be configured to transmit body-related metrics electronically to the monitoring application 136 on the mobile device 135. In turn, the monitoring application 136 sends the captured metrics to the workflow server 110 which can be used to trigger health events which are processed using the processing nodes 114 and the queues 115.

In one embodiment, upon detecting an observation threshold has been reached, the at least one sensor device 140 performs an initial classification of the health event. In a particular embodiment, the mobile device 135 is configured to perform the initial classification of the health event. For example, the body sensor 141, upon detecting that ECG data collected from the patient 103 indicates an erratic heart behavior, could classify the health event as a cardiac event. This initial classification of the health event, along with the relevant ECG data (e.g., ECG data including a predetermined length of time before and after the event), could be transmitted to the mobile device 135 (e.g., over a Bluetooth® communications link) and the monitoring application 136 subsequently forwards the ECG data and the health event data on to the workflow server 110 over the network 145 (e.g., the Internet). Alternatively, instead of classifying the data, the monitoring application 136 may forward the raw, unprocessed sensor data to the event manager 110 which uses one of the processing nodes 114 to identify and classify health events which are then processed in the workflow server 110.

Figure 2:
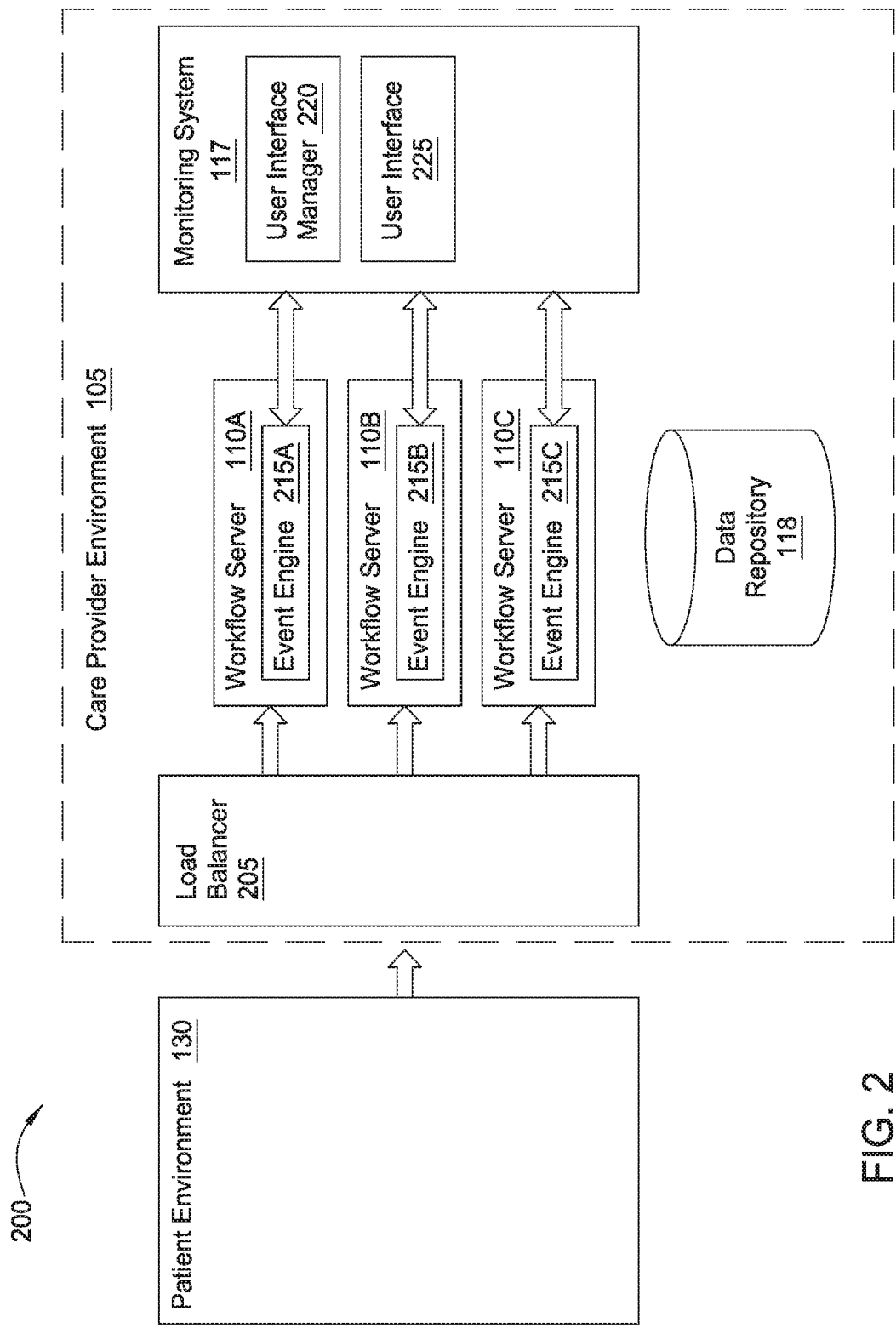
FIG. 2 illustrates a parallel processing computing environment, according to one embodiment.

FIG. 2 illustrates a parallel processing computing environment 200, according to one embodiment. As shown, the patient environment 130 transmits biometric data and/or health events to the care provider environment 105 which includes a load balancer 205. The workflow servers 110A-110C each include a respective one of the event engines 215A-215C. Although not shown, each of the event engines 215A-215C includes a plurality of interconnected processing nodes and queues that form a workflow for processing health events as discussed above. In one embodiment, the event engines 215A-215C each includes the same processing nodes and queues arranged in the same manner such that any one of the event engines 215A-215C can process the different health events generated by the at least one sensor device 140—i.e., any one of the event engines 215A-215C can process a cardiac event, respiratory event, maintenance event, etc. Based on current workload, the load balancer 205 transmits received data or heath events to one of the workflow servers 110A-110C for processing. For example, the load balancer 205 may assign the received health events in a round robin manner or by monitoring each respective central processing unit (CPU) or memory usage of the workflow servers 110A-110C.

Alternatively, the event engines 215A-215C may have different processing nodes and queues (or a different arrangement of the nodes and queues) such that the event engines 215A-215C are configured to process different event types. For example, the event engines 215A, 215B may have workflows that process cardiac events (and have the same processing nodes and queues), while the workflow in the event engine 215C processes respiratory events. The load balancer 205 may determine which of the event engines 215A-215C should receive the health event using the initial classification provided by the patient environment 130 or based on which of the at least one sensor device 140 measured the biometric data.

Regardless whether the event engines 215A-215C have the same arrangement or different arrangements, compute resources can easily be adjusted in response to varying workloads. For example, additional ones of the at least one sensor device 140 are added to the patient environment 130, a system administrator can add additional ones of the workflow servers 110A-110C to process an increased number of received health events. The reverse is also true. If the number of health events decreases, the administrator may remove one or more of the workflow servers 110A-110C. For example, if the event engines 215A, 215B both process cardiac events but the number of cardiac events has decreased, the system administrator may remove one of the workflow servers 110A, 1108.

With continued reference to FIG. 2, the monitoring system 117 includes a user interface manager 220 (UI manager) and a user interface 225 (UI). As discussed above, the processing nodes 114 may require input from the care provider 101 (FIG. 1) in order to route the health events through the event engines 215A-215C. To do so, the event engines 215A-215C transmit requests to the UI manager 220 which generates the UI 225 which can be displayed to the care provider 101. For example, the UI manager 220 may generate the UI 225 that includes an electrocardiogram (ECG) chart corresponding to a cardiac event. Further, the UI 225 may include I/O features (e.g., buttons or pull down menus) that the care provider can use to provide input or instructions to one of the event engines 215A-215C. For example, the care provider may instruct the one of the event engines 215A-215C to store the cardiac event in the data repository 118, send the cardiac event to one of the queues 115 (FIG. 1) that is monitored by another care provider (e.g., to get a second opinion), or forward the cardiac event to the care provider 101 of the patient 103. Thus, the monitoring system 117 permits the workflow servers 110 to output information to the care provider 101 as well as receive instructions from the care provider 101.

The event engines 215A-215C may store data in and retrieve data from the data repository 118. For example, the event engines 215 may maintain a patient history by storing all the received health events (or selected health events) derived based on monitoring a patient's vitals in the repository 118. Further, the event engines 215A-215C may use the data stored in the data repository 118 to process the health events. For example, if one of the event engines 215A-215C receives biometric data indicating the current weight of the patient 103, then the one of the event engines 215A-215C can retrieve past weight measurements for the patient 103 from the data repository 118 and derive a trend graph detailing how the weight of the patient 103 has changed over time. For instance, the patient's current weight may not be enough to trigger a health event, but the patient's derived weight change over a period of time may trigger a health event. As discussed below, these derived trends may be used to generate a derived observation.

In one embodiment, the event engines 215A-215C prioritize health events, which, in turn, determines how quickly the health events are processed by the workflows in the event engines 215A-215C or what processing nodes and queues are used to process the health events. As discussed above, the health events may be prioritized based on a severity of the health event, the type of the health event, a characteristic of the patient 103 whose biometric data generated the health event, and the like.

Figure 3:
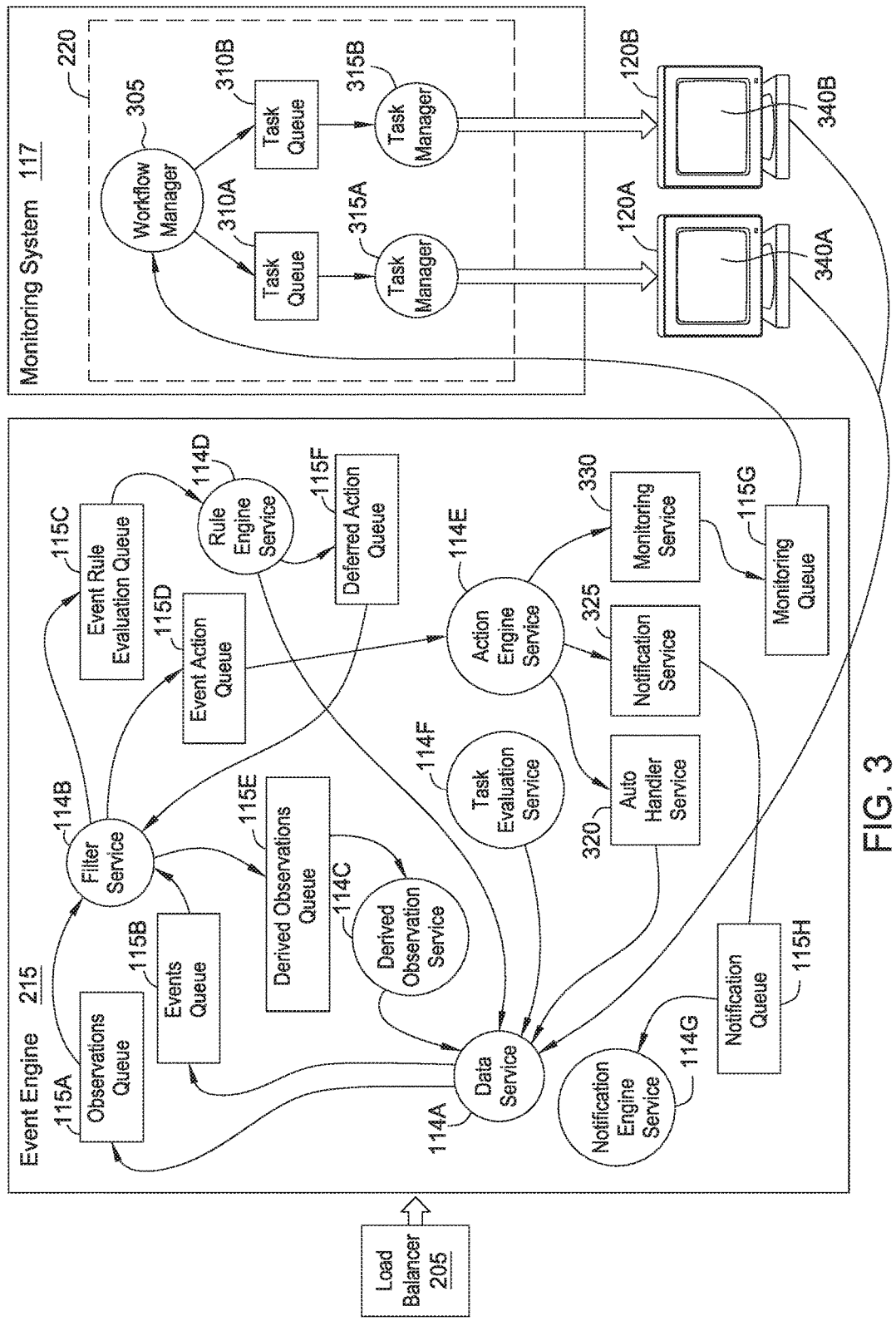
FIG. 3 illustrates an event engine for processing received health events, according to one embodiment.

FIG. 3 illustrates one of the event engines 215A-215C, depicted generically as an event engine 215, including a workflow for processing health events, according to one embodiment. As described above, a health event or biometric data received from the at least one sensor device 140 (FIG. 1) is forwarded from the load balancer 205 to the event engine 215. Specifically, a data service node 114A in the workflow receives the forwarded information from the load balancer 205. If the load balancer 205 forwards a health event, the data service node 114A classifies the health event based on type (e.g., a cardiac, respiratory, or maintenance event). In some cases, the health event was classified before being received by the data service node 114A. Nonetheless, the data service node 114A may review the data associated with the health event such as ECG data, breathing rate, blood pressure, etc. using more compute intensive techniques to determine whether the initial classification was correct. In another example, the data service node 114A may provide a more detailed classification of the health event than the initial classification. For example, the at least one sensor device 140 may have generated the health event because it detected an irregular heartbeat. However, the data service node 114A may evaluate the heartbeat and classify the health event as a specific cardiac health event—e.g., a ventricular trigeminy event or an atrioventricular block event. The data service node 114A may save the classification of the health event which is used by downstream nodes and queues to process the health event.

Instead of receiving a health event, the data service node 114A may receive raw data or observations from the patient environment 130. That is, the raw data or observations may not have been evaluated by the at least one sensor device worn by the patient to determine if this data triggers a health event. For example, observation data from a sensor includes blood pressure measurements, weight measurements, ECG data, and the like. As discussed below, the event engine 215 evaluates these observations and can trigger health events which are then processed in the engine 215.

With continued reference to FIG. 3, the data service node 114A forwards the observations to the observation queue 115A and the health events to the events queue 115b. A filter node 114b pulls the observations and health events stored in the queues 115A and 115B. This node 114B serves as a gatekeeper that determines where the health events and observations are routed for further processing. When evaluating observations, the filter node 114B may determine whether to ignore (i.e., drop) the observations or forward the observations to a derived observation queue 115E. For example, observations such as low battery signals, start signals indicating the at least one sensor device 140 has started collecting biometric data, or stop signals indicating the at least one sensor device 140 has stopped may be ignored by the filter service node 114b. In contrast, the node 114B may forward observations such as weight measurements, blood pressure measurements, ECG data, and the like to the derived observation queue 115E. In this manner, the filter service node 114B screens the incoming observations to determine whether they should be processed further such as checking for triggering health events.

Observations forwarded by the filter service node 114B are then processed by a derived observation service node 114C. This derived observation service node 114C uses received observations in conjunction with previously received observations to create new observations or to generate a new health event. Stated differently, the derived observation service node 114C may aggregate previously received observations with the currently received observations to compute statistics, trends, trigger health events, and the like. Although not shown, the derived observation service node 114C may be communicatively coupled to the data repository which stores past observations. For example, if the currently received observation is a weight measurement, the derived observation service node 114C may evaluate this measurement with previous weight measurements to determine a weight change for the patient over a defined period of time. This weight change may trigger a health event which is then forwarded to the data service node 114A for further processing. Even if a health event is not triggered, the derived observation service node 114C may store a derived observation (e.g., a weight change, average blood pressure, heart rate trends, etc.) in the data repository so that this data is available when further observations for the patient are received by the event engine 215 (or other event engines 215).

In one embodiment, health events may be processed by the derived observation service node 114C. For example, one of the at least one sensor device 140 may trigger a health event upon determining a patient's average blood pressure for a day exceeds a threshold. The filter service node 114B may forward this health event to the derived observation service node 114C which then may use past blood pressure measurements for that patient 103 to derive a weekly or monthly average blood pressure for the patient 103, or a blood pressure trend graph. Based on this derived observation, the derived observation service node 114C may generate a new health event or decide to drop the health event if the derived observation does not satisfy a corresponding condition.

Further, the filter service node 114B also includes logic for determining whether received health events should be dropped, forwarded to an event action queue 115D, or forwarded to the event rule evaluation queue 115C. For example, a system administrator may determine that some health events are not relevant for certain patients. The logic in the filter service node 114B may identify and drop these health events to prevent them from propagating through the rest of the event engine 215. For instance, a patient may have a heart murmur that constantly results in a sensor device triggering a health event. Rather than continually processing these health events, the care provider 101 can instruct the filter service node 114B to screen out (or suppress) these health events from the patient 103.

If a received health event has a corresponding action or actions, the filter service nodes 114B forwards the health event to the event action queue 115D. However, if the action for a health event has not yet been identified, the filter service node 114B forwards the health event to the event rule evaluation queue 115C. A rule engine service node 114D pulls the health events from the queue 115C and evaluates the health event using one or more rules. An example of the one or more rules includes determining whether daily weight change and average blood pressure exceed respective thresholds. Based on this evaluation, the rule engine service node 114D may determine what action the event engine 215 should perform—e.g., suppress/ignore the event, auto handle the event, display the event to a care provider, or delay processing the event. Once the action is determined, the rule engine service node 114D generates and forwards a new health event that includes the corresponding action to the data service node 114A. Now that the corresponding action is known, once the new health event reaches the filter service node 114B, it forwards the health event to the event action queue 115D rather than the event rule evaluation queue 115C.

With continued reference to FIG. 3, the rule engine service node 114D may delay processing the health event by forwarding the health event to a deferred action queue 115F. The rule engine service node 114D may do so when there is not enough available computing power to perform the rule evaluation or if the rule evaluation has not yet completed. That is, if all of the rules have not yet been evaluated and further evaluation is required before triggering the event action, then the health event may be placed in the deferred action queue 115F. For example, the rule may trigger a cardiac event but the monitoring system 117 must first check to determine if that health event is suppressed for the patient 103 before taking the corresponding action. As shown, the health events stored in the deferred action queue 115F are then retrieved by the filter service node 114B and can be reintroduced into the event rule valuation queue 115C at a later time—i.e., when all the rules have been evaluated.

Once a corresponding action for a health event is known and the health event is stored in the event action queue 115D, an action engine service node 114E routes the health event to the appropriate action service—i.e., auto handler service 315, notification service 320, or monitoring service 325. The auto handler service 315 may perform actions that do not require supervision or input by a care provider—e.g., stores the health event in the data repository. As another example, the auto handler service 320 may assign a priority or severity to the health event before the event is reintroduced into the workflow with the new priority. The auto handler service 320 may also generate a new health event when, for example, a health event shows a cardiac event but the data quality is low. In response, the auto handler service 320 may introduce a maintenance event for checking the sensor connection/electrodes.

With continued reference to FIG. 3, the event engine 215 uses notification service 325 to send information to the patient 103, the care provider 101, or the at least one sensor device 140 regarding the health event. The notification service 325 may include different communication channels or techniques for communicating with the patient such as email, chat, SMS messages, etc. Although FIG. 3 illustrates only one notification queue 115H and notification engine service node 114G for handling requests, the event engine 215 may have different queues and notification nodes for the different communication techniques. For example, if a maintenance event is triggered when an electrode is unplugged from the at least one sensor device 140, then the notification service 325 may transmit an email to the patient's mobile device instructing the patient to plug in the electrode. Alternatively, if a respiratory event is triggered because of an elevated breathing rate, the notification service may send an SMS message to the patient 103 asking her if she is currently performing a physical activity.

The event engine 215 also includes a task evaluation service node 114F. Unlike the other nodes and queues in event engine 215 which process or store observation data or health events received from the patient environment, the task evaluation service node 114F determines whether to trigger a health event based on a care protocol or care plan. In one embodiment, the node 114F triggers a health event when the patient does not follow the care protocol or plan. For example, the care protocol may ask that the patient wear one of the at least one sensor device 140 for certain amount of time during the day or take weight measurements each day. By monitoring the observation and health events received by the event engine 215, the task evaluation service node 114F determines whether the patient 103 has complied with the care protocol. If not, the task evaluation service node 114F triggers a health event with a corresponding action for the event engine 215 to perform such as sending a notification to the patient 103 using notification service 325 or informing a care provider using a monitoring service 330.

The monitoring service 330 communicatively couples the event engine 215 to the monitoring system 117. When input from a care provider regarding a health event is desired, the monitoring service 330 forwards the health event to a monitoring queue 115G. The UI manager 220 in the monitoring system 117 includes a workflow manager node 305 that pulls health events from the monitoring queue 115G and assigns them to either a task queue 310A or a task queue 310B. The UI manager 220 also includes task manager node 315A and task manager node 315B which generate UIs for the health events. These UIs are then displayed to care providers 101 via the at least one computing device 120A and 120B. Further, the task manager nodes 315A, 315B may place the biometric or maintenance data associated with the health events in the UIs. For example, a UI for a cardiac event may display an ECG graph and a baseline chart, while a UI for respiratory event displays a breathing rate and oxygen levels in the blood. In this manner, the UI manager 220 can generate a customized UI for the different health events.

The at least one computing device 120A, 120B may transmit information to the data service node 114A of the event engine 215 which can be used to generate new health events or update current health events. For example, the care provider 101 may instruct the event engine 215 to take a certain action such as forwarding the health event to a different care provider to get a second opinion, reclassifying the health event, suppressing or ignoring the health event, notifying a health care provider, and the like. Based on the care provider's input, the event engine 215 again routes the health event through the nodes 114 and queues 115.

The user interfaces 340A, 340B (UIs) respectively output on the computing devices 120A, 120B can be generated to enable the care provider 101 to easily recognize correlations between health events (e.g., ECG events) and a monitored health metric (e.g., a patient's average heart rate over a period of time). The ability to easily identify groups of the health events as well as understand the time that the health event occurred can better enable the care provider 101 to accurately diagnose a condition of the heart of a patient 103 and thereby provide a more effective treatment.

Figure 4:
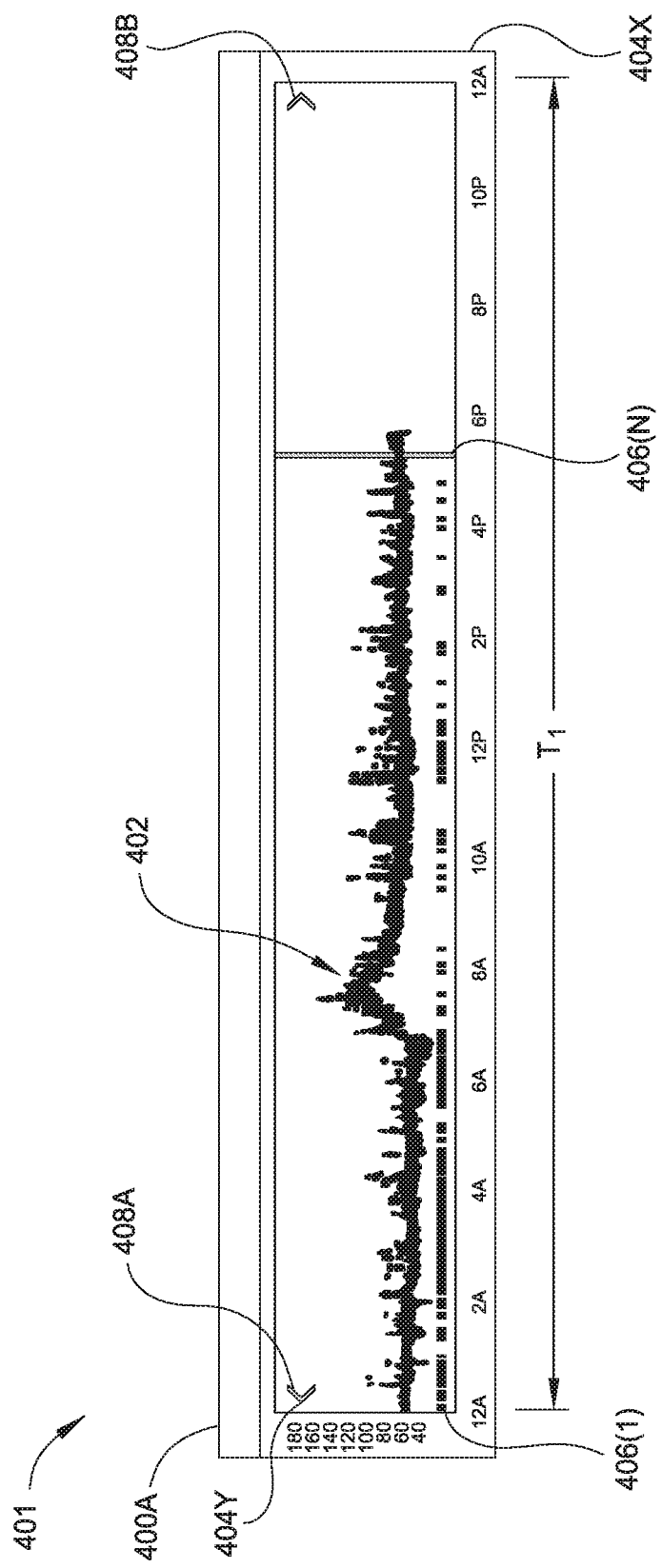
FIG. 4 is a first graph of an exemplary user interface, according to one embodiment.

In this regard, FIG. 4 is a first graph 400A of an exemplary user interface 401. For instance, the user interface 401 may be utilized as a portion of one of the user interfaces 340A, 340B depicted in FIG. 3. The first graph 400A includes heart rate data 402 measured in an ordinate axis 404Y as a function of time as part of a first time window T1 in an abscissa axis 404X. The time window T1 has a 24-hour duration from 12 AM one day to 12 AM the next day in the depicted embodiment. For instance, the time window T1 may be predetermined by program defaults in the monitoring system 117 or selected by the care provider 101. The first graph 400A includes multiple health event indicators 406(1)-406(N), with each health event indicator 406 representing a respective health event having a time of occurrence. The health event may be determined, as discussed above, at the at least one sensor device 140 or in the workflows of the event engines 215A, 215B, 215C. Generally, the quantity N of the health event indicators 406(1)-406(N) represents the number of events detected for a given patient during the time window T1.

The health events are placed on the first graph 400A based on the time each respective health event occurred. Likewise, the heart rate data 402 is positioned on the graph 400A based on the time each measure of heart rate data 402 was measured. The health event indicators 406(1)-406(N) are aligned parallel to the abscissa axis 404X and offset from the heart rate data 402 for ease of viewing. The time of occurrence of each health event is used to determine the location of the respective one of the health care indicators 406(1)-406(N) with respect to positions along the abscissa axis 404X. For example, health event indicator 406(1) is associated with a time of occurrence of 12:10 AM and is disposed on a geometric line (not shown) which is orthogonal to a 12:10 AM position on the abscissa axis 404X and the health event indicator 406(N) is associated with a time of occurrence of 5:30 PM and is disposed on a second geometric line (not shown) which is orthogonal to a 5:30 PM position on the abscissa axis 404X. In this manner, the temporal relationship between the health events and the heart rate data 402 can be depicted efficiently in the first graph 400A.

In the depicted embodiment, the 24-hour span of the time window T1 enables the care provider 101 to look for patterns in the heart rate data 402 during this time while comparing against relative occurrences of the health events. In the exemplary data shown in the first graph 400A, a large quantity of health events occurring from 2 AM to 7 AM precedes the heart rate increase that occurs at 7 AM. By depicting heart rate data for the patient alongside the detected events, the first graph 400A enables care providers 101 to more efficiently interpret the patient's event data and to make correlations between health events and heart rate data. For example, the care provider 101 could determine that the clusters of health events appearing at 10 AM and 12 PM on the graph 400 merit investigation by the care provider 101. It is briefly noted that the first graph 400A may also include navigation arrows 408A, 408B to enable the health care provider to time shift the heart rate data 402 depicted on the first graph 400A respectively to values occurring before or after the time window T1 for further data analysis by the care provider 101.

Generally, the first graph 400A enables the care provider to quickly ascertain areas of anomalies (e.g., false positive and false negative events) within a window of patient data. For example, in the case of a false positive anomaly, the first graph 400A enables the provider to visualize and compare clusters (i.e., high concentrations) of health events with the patient's heart rate. For instance, if the care provider sees that the patient has a relatively low heart rate during a period of time that includes a high concentration of the health events, the care provider could determine that the high concentration of events presents a high risk situation, as the patient is experiencing a substantial number of events during a period of relatively low activity (e.g., while the patient is sleeping). On the other hand, the care provider could use the first graph 101 to observe that no events occurred during a substantial window of time, which could be an indication that the system monitor 117 or a sensor device 140 has a loose wire or otherwise is not reporting events to the server.

In one embodiment, the monitoring system 117 includes pattern recognition logic that is configured to detect predefined patterns and/or correlations between health events and health metrics (e.g., heart rate data) for a given patient. For instance, the pattern recognition logic could be configured to analyze a patient's data to detect (without limitation) the situations described above, namely, where a substantial number of events are detected during a period of relatively low activity and where no events are detected during a substantial period of time. More generally, however, any recognizable correlation can be detected by the pattern recognition logic, consistent with the present disclosure. Upon detecting a predefined pattern or correlation, the pattern recognition logic could mark the detected pattern or correlation in the user interface 401. For example, the pattern recognition logic could outline the area of the graph 400A containing the detected pattern or correlation in dashed lines, or could otherwise provide graphical (or otherwise) feedback to alert the care provider 101 that a predefined pattern or correlation has been detected at the first graph 400A.

Of note, while the aforementioned examples depict heart rate and ECG data within the user interface, more generally any vital data metrics that a health care provider wishes to correlate could be depicted within the graphs. Moreover, any number of different vital data metrics could be depicted within the same graph, consistent with the functionality described herein. For example, a health care provider could configure to depict heart rate, ECG data and blood pressure data values for a particular patient within the user interface. More generally, any number and type of vital data metrics can be used.

Figure 5:
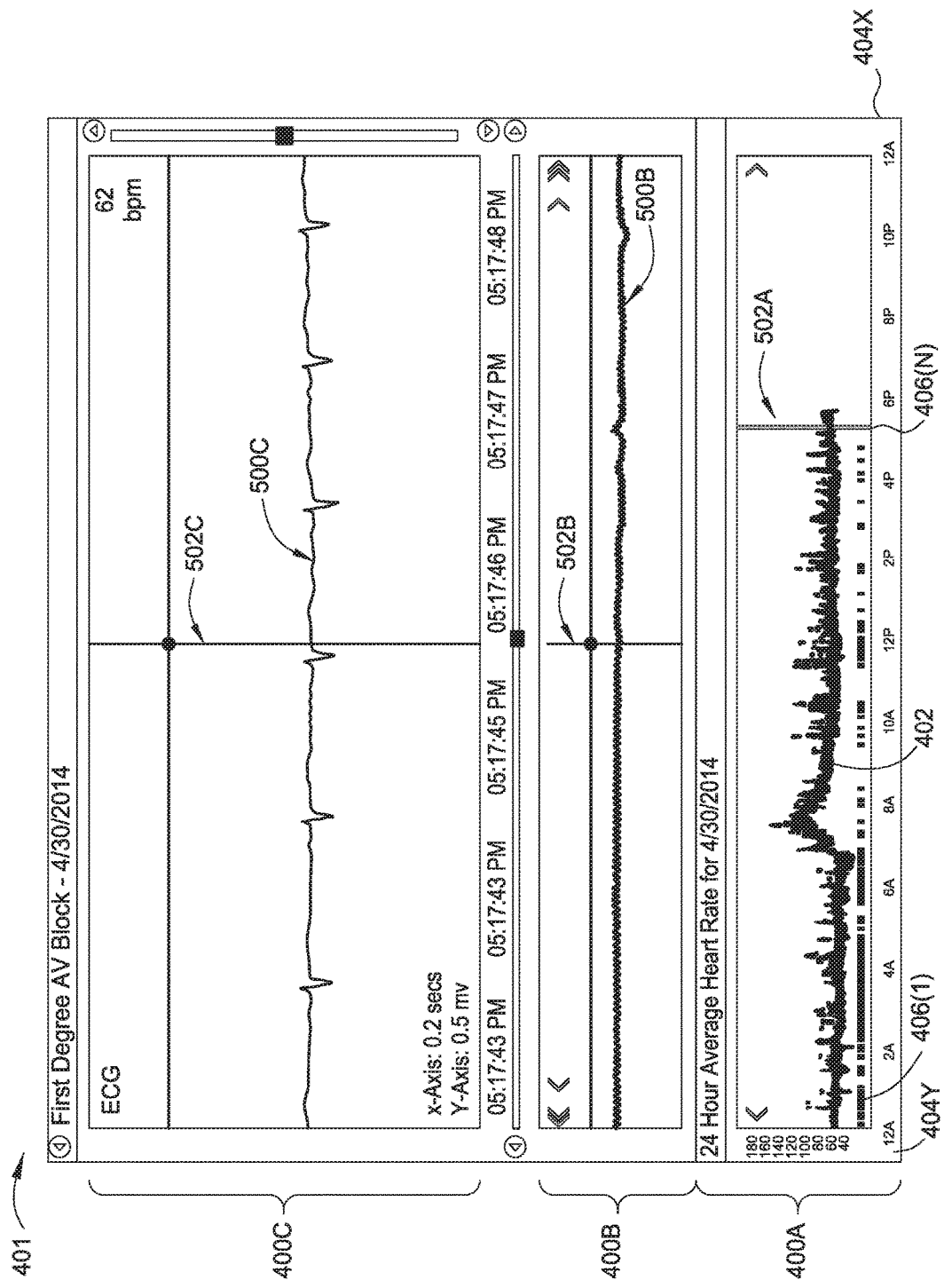
FIG. 5 is the first graph of the user interface of FIG. 4 disposed adjacent to second and third graphs of the user interface, according to one embodiment.

FIG. 5 illustrates the first graph 400A of the user interface 401 of FIG. 4 disposed adjacent to a second graph 400B and a third graph 400C of the user interface 401. The second graph 400B and the third graph 400C depict electrocardiogram data 500B, 500C over a two (2) minute interval and a six (6) second interval respectively. Of course, one of ordinary skill in the art will recognize that the six (6) second and two (2) minute intervals are provided for illustrative purposes only and that, more generally, intervals of any duration may be used. Moreover, the intervals could be set using various techniques. For example, the intervals could be initially set using default values (e.g., 2 minutes and 6 seconds, respectively) and could then be adjusted based on user input. As another example, the intervals could be set based on data specifying a health care organization's best practices. And as yet another example, the intervals may be adjusted automatically based on the data type, the density of the data, or by learning that the interval is frequently changed to specific settings. It is recognized that the intervals may also be adjusted to different values according to best practices of the facility where the data is being analyzed or by the preferences of the care provider 101 on a case-by-case basis.

The second graph 400B and the third graph 400C are temporally associated with the first graph 400A by use of a vertical selector 502A in the first graph 400A. A position of the vertical selector 502A along the abscissa axis 404X can be changed according to actions of the care provider 101 (e.g., selecting a position on the graph 400A using an input device such as a mouse or touchscreen). The currently selected position 502A, shown as 5:17 PM in FIG. 5, is associated with respective positions of vertical selectors 502B, 502C in the second graph 400B and the third graph 400C. The vertical selector 502B may be disposed in the second graph 400B at the 5:17 PM position within the electrocardiogram data 500B with halves of the two (2) minute interval disposed at opposite sides of the vertical selector 502B. Similarly, the vertical selector 502C may be disposed in the third graph 400C at the 5:17 PM position within the electrocardiogram data 500C with halves of the six (6) second interval disposed at opposite sides of the vertical selector 502C. In this manner, the first, second and third graphs 400A-400C can be temporally related.

Figure 6:
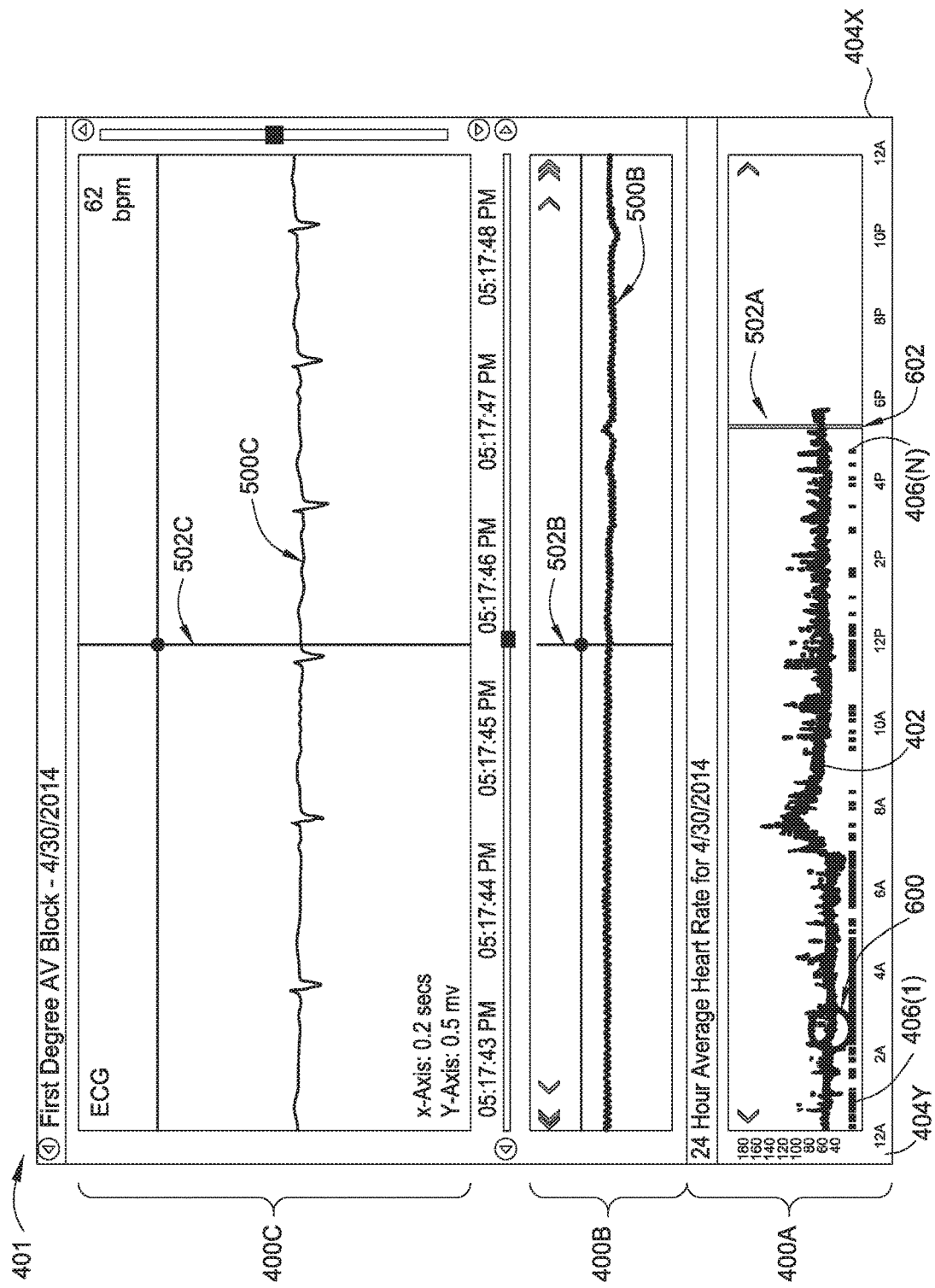
FIG. 6 is the exemplary interface of FIG. 5 depicting the first, the second, and third graphs wherein a second selected time is identified, according to one embodiment.

Generally, the care provider 101 can change the position of the vertical selector 502A to a new position (e.g., by selecting a position on the graph 400A using an input device). Upon changing the position of the vertical selector 502A to the new position, the graphs 400B and 400C can be automatically updated to depict the ECG data surrounding the new position. An example of this is shown in FIG. 6, which depicts an exemplary new desired time 600 at 2:47 AM which is different from the 5:17 PM position where the vertical selector 502A is positioned in FIG. 5. In one embodiment, a cursor 602 (FIG. 6) may be used to move the vertical selector 502A to the new desired time 600 at 2:47 AM or alternatively in another embodiment the care provider 101 may click the first graph 400A at or near the desired time 600 to move the vertical selector 502A to the new desired time 600. Other conventional ways of changing the position of the vertical selector 502A may be utilized as may be known for moving objects within a user interface.

Figure 7:
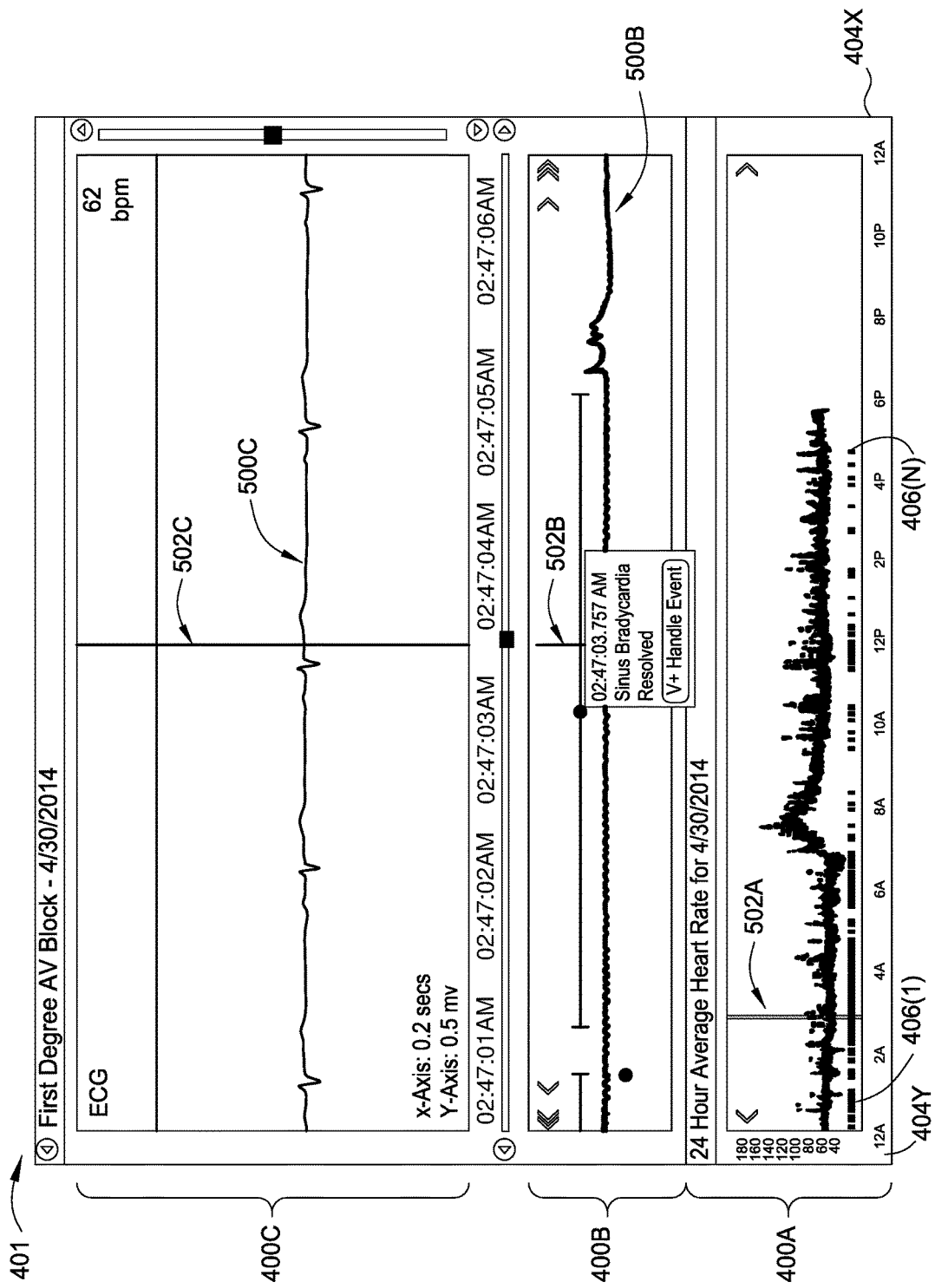
FIG. 7 is the exemplary interface of FIG. 6 depicting the first, the second, and third graphs wherein the second selected time is chosen by a user, according to one embodiment.

In this regard, FIG. 7 is the user interface 401 of FIG. 6 wherein the vertical selector 502A is moved to the new desired time 600 at 2:47 AM. Upon a change in the position of the vertical selector 502A, the second graph 400B and the third graph 400C are updated to reflect the new desired time 600 at 2:47 AM. Specifically, the vertical selector 502B may be disposed in the second graph 400B at the 2:47 AM position within the electrocardiogram data 500*b* with halves of the two (2) minute interval disposed at opposite sides of the vertical selector 502B. Similarly, the vertical selector 502C may be disposed in the third graph 400C at the 2:47 AM position within the electrocardiogram data 500C with halves of the six (6) second interval disposed at opposite sides of the vertical selector 502C. In this manner, the first, second and third graphs 400A-400C can be temporally updated to reflect the position of the vertical selector 502A in the first graph 400A.

Movement of the vertical selector 502A within the first graph 400A and subsequent updates of the second graph 400B and the third graph 400C in response to the movement enable the care provider to conduct efficient research into the condition of the patient 103. Specifically, the care provider 101 may efficiently research the relationship between the electrocardiogram data 500B, the electrocardiogram data 500C, the heart rate data 402, and the health event indicators 406(1)-406(N). It is recognized that monitoring system 117 may represent all or a portion of the health events as the health care indicators 406(1)-406(N) depending upon severity or type of event. The health care indicators 406(1)-406(N) may also be modified based on severity or type using various colors or shapes as provided at the user interface 401. In this manner, the care provider 101 may more efficiently discern the meaning of the various events and respond to the needs of the patient 103.

Figure 8:
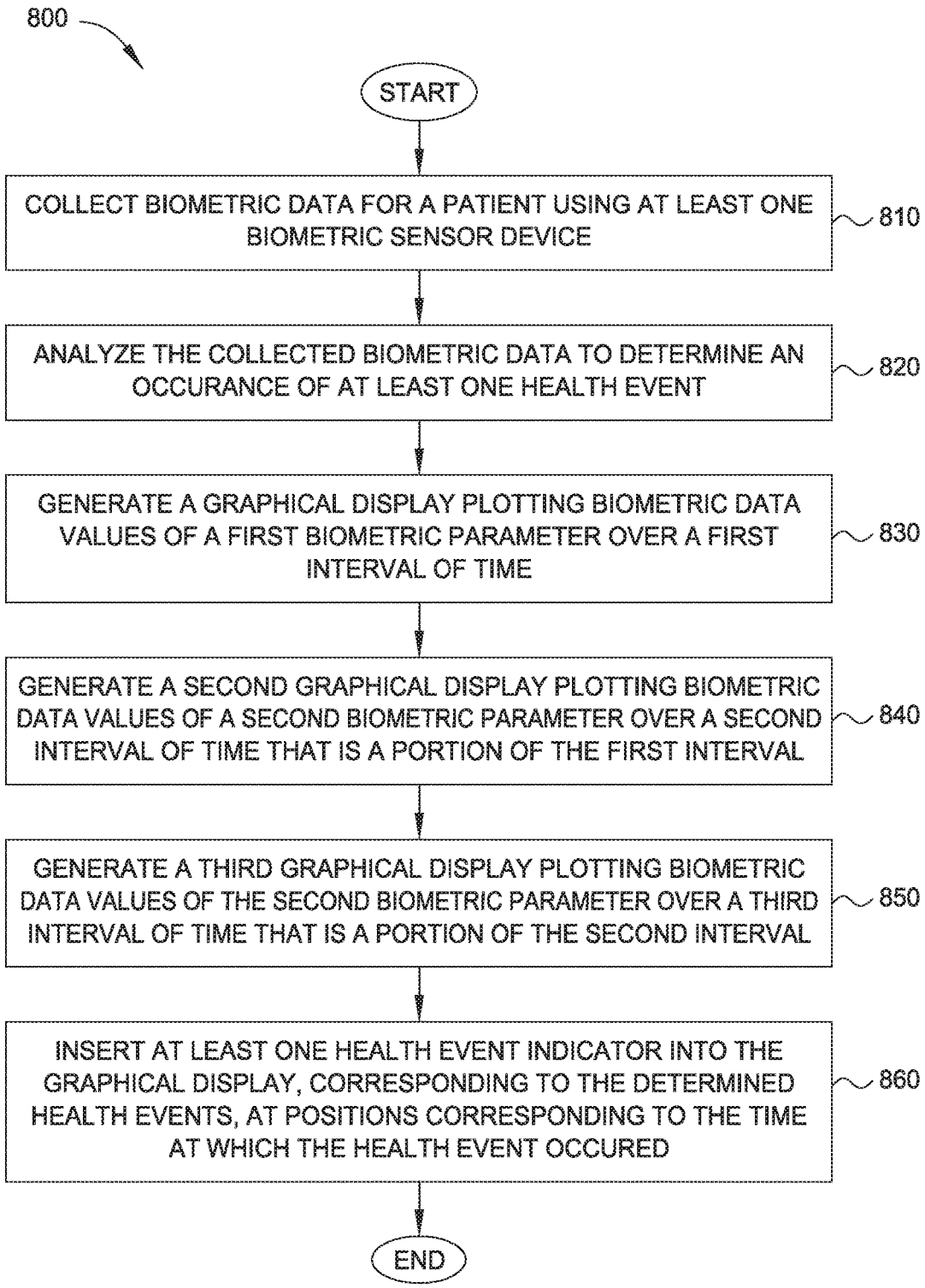
FIG. 8 is a flowchart of an exemplary process for displaying a temporal relationship between a health event and a monitored health condition, according to one embodiment.

FIG. 8 is a flowchart of an exemplary process 800 for displaying a temporal relationship between health events and monitored health conditions in the user interface 401, according to one embodiment. The method 800 includes collecting biometric data for a patient using at least one biometric sensor device (operation 810 of FIG. 8). The collected biometric data can be analyzed to determine occurrences of one or more health events (operation 820 of FIG. 8). At block 830, logic on the monitoring system 117 generates a graphical display plotting biometric data values of a first biometric parameter (such as heart rate) over a first interval of time. The logic on the monitoring system 117 also generates a second graphical display plotting biometric data values of a second biometric parameter (such as ECG data) over a second interval of time that is a portion of the first interval of time (operation 840 of FIG. 8). Additionally, the logic generates a third graphical display plotting biometric data values of the second biometric parameter over a third interval of time that is a portion of the second interval (operation 850 of FIG. 8). At operation 860, the logic inserts at least one heath event indicator into the graphical display, corresponding to the determined health events, at positions corresponding to the time at which each health event occurred.

Figure 9:
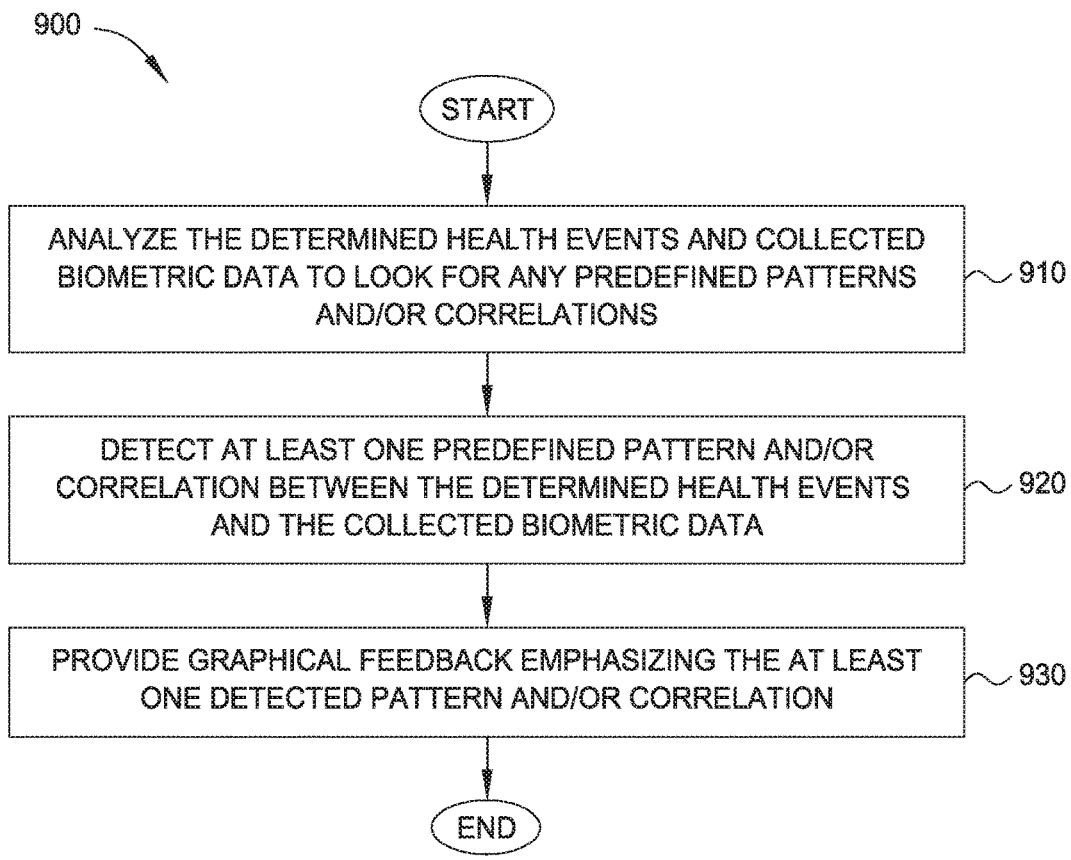
FIG. 9 illustrates a computing environment for processing health events, according to one embodiment.

FIG. 9 is a flowchart of an exemplary process 900 for providing visual feedback of predefined patterns and correlations. The method 900 includes analyzing the determined health events and collected biometric data to identify predefined patterns between the two (operation 910 of FIG. 9). The logic on the monitoring system 117 detects at least one predefined pattern or correlation between the determined health events and the collected biometric data at 920. The logic also provides graphical feedback to emphasize the detected at least one pattern or correlation (operation 930 of FIG. 9).

Figure 10:
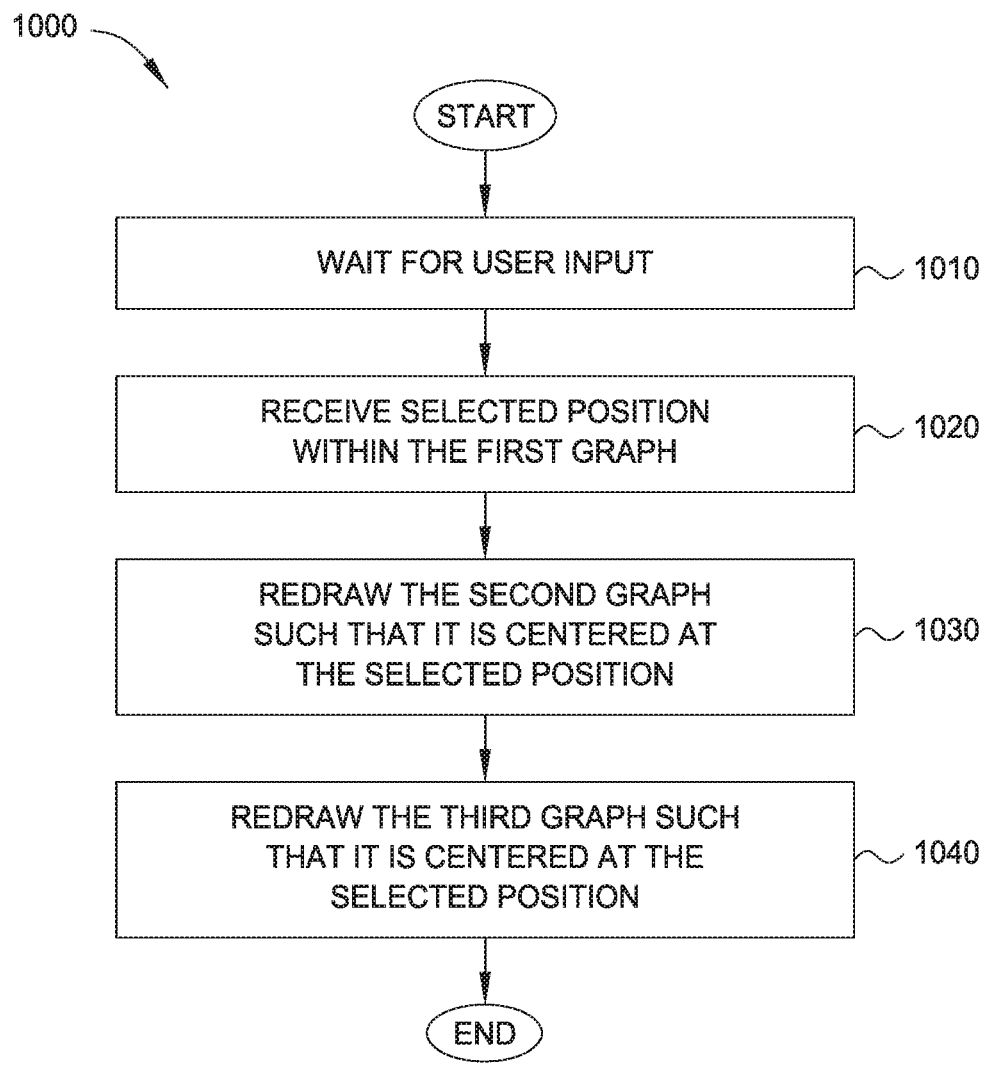
FIG. 10 is a flowchart of an exemplary process 1000 for adjusting the user interface in response to user input, according to one embodiment.

FIG. 10 is a flowchart of an exemplary process 1000 for adjusting the user interface in response to user input, according to one embodiment. The logic on the monitoring system 117 waits for user input (operation 1010). The logic receives a selected position within the first graph (operation 1020) and redraws the second graph such that it is centered at the selected position (operation 1030 of FIG. 10). Further, the logic redraws the third graph such that it is centered at the selected position (operation 1040 of FIG. 10).

Figure 11:
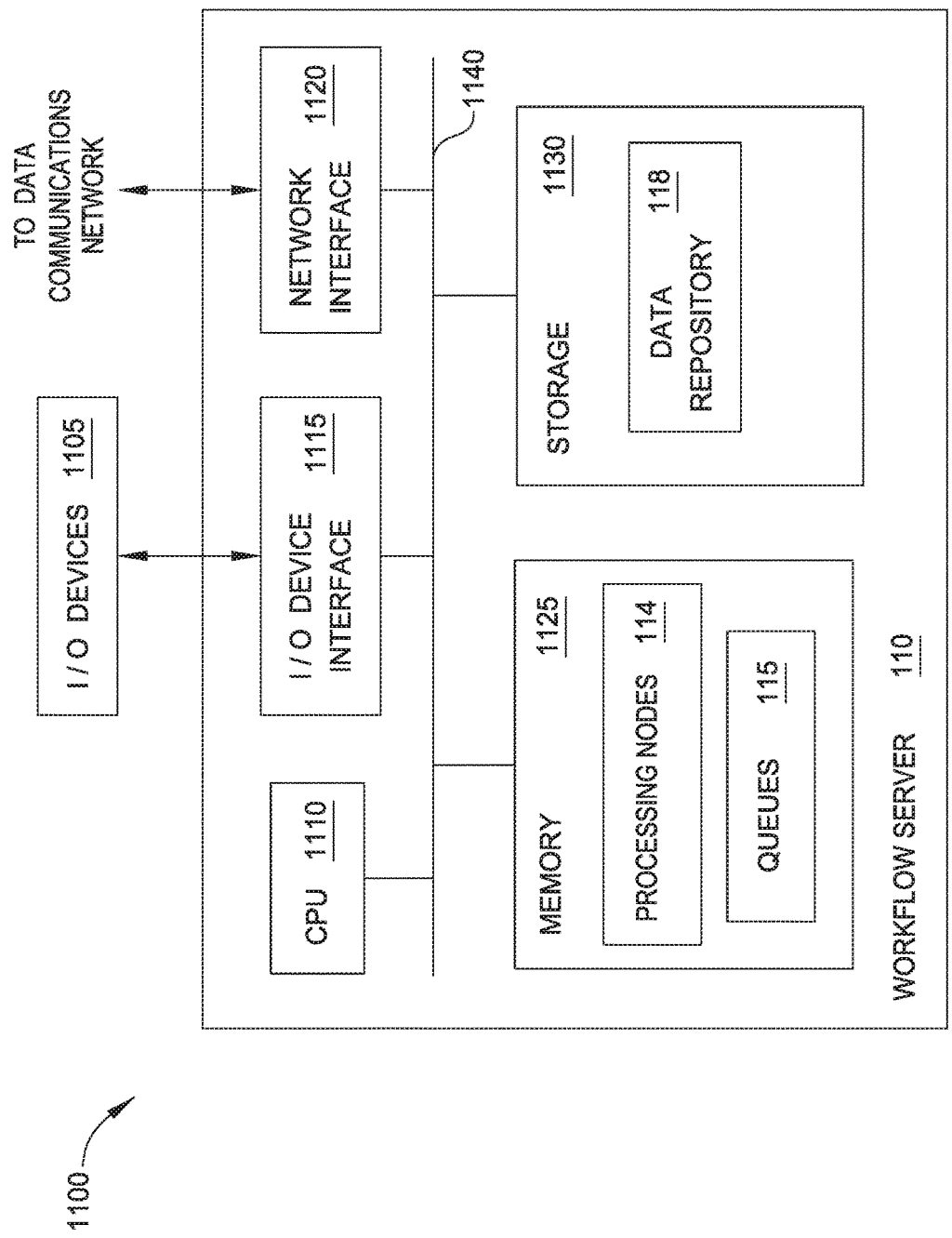
FIG. 11 illustrates a computing environment 1100 for processing health events, according to one embodiment.

FIG. 11 illustrates a computing environment 1100 for processing health events, according to one embodiment. As shown, workflow server 110 includes, without limitation, a central processing unit (CPU) 1110, a network interface 1120, a memory 1125, and storage 1130, each connected to a bus 1140. The workflow server 110 may also include an I/O device interface 1115 connecting I/O devices 1105 (e.g., keyboard, display and mouse devices) to the environment 110. Further, in context of this disclosure, the computing elements shown in the workflow server 110 may correspond to a physical computing system (e.g., a system in a data center) or may be a virtual computing instance executing within a computing cloud.

CPU 1110 retrieves and executes programming instructions stored in the memory 1125 as well as stores and retrieves application data residing in the storage 1130. The bus 1140 is used to transmit programming instructions and application data between the CPU 1110, the I/O devices interface 1115, the storage 1130, the network interface 1120, and memory 1125. Note, CPU 1110 is included to be representative of a single CPU, multiple CPUs, a single CPU having multiple processing cores, and the like. The memory 1125 is generally included to be representative of a random access memory. The storage 1130 may be a disk drive storage device. Although shown as a single unit, the storage 1130 may be a combination of fixed and/or removable storage devices, such as fixed disc drives, removable memory cards, network attached storage (NAS), or a storage area-network (SAN).

Illustratively, the memory 1125 includes the processing nodes 114 and queues 115, while storage 1130 includes the data repository 118. The processing nodes 114 may be assigned to the same CPU 1110 or to different CPUs. Further, each processing node 114 may include respective sets of consumers (e.g., processes or threads) that are assigned to process different priority health events. The consumers monitor upstream queues 115, and when idle, retrieve and process health events that are assigned the same priority level.

In the preceding, reference is made to embodiments presented in this disclosure. However, the scope of the present disclosure is not limited to specific described embodiments. Instead, any combination of the described features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s).

As will be appreciated by one skilled in the art, the embodiments disclosed herein may be embodied as a system, method or computer program product. Accordingly, aspects may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium is any tangible medium that can contain, or store a program for use by or in connection with an instruction execution system, apparatus or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments presented in this disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality and operation of possible implementations of systems, methods and computer program products according to various embodiments. In this regard, each block in the flowchart or block diagrams may represent a module, segment or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In view of the foregoing, the scope of the present disclosure is determined by the claims that follow.

We claim:

1. A method of generating a user interface for monitoring biometric data collected by monitoring a user, comprising:
generating a first portion of the user interface by plotting a first plurality of values of a first biometric parameter of a first type of biometric parameter on a first graph structure with respect to a first interval of time;
generating a second portion of the user interface by plotting a second plurality of values of a second biometric parameter of the first type of biometric parameter on a second graph structure with respect to a second interval of time that overlaps with only a portion of the first interval of time;
receiving a plurality of health events, the health events previously determined by classifying a second type of biometric parameter received by a monitoring device;
inserting a plurality of indications of the health events into the first graph structure;
detecting, using pattern recognition logic executing on a processor, a predefined pattern between the first plurality of values and the plurality of previously determined health events, wherein the first plurality of values is the first type of biometric parameter received by the monitoring device, and wherein the first type of biometric parameter is different from the second type of biometric parameter;
providing graphical feedback to indicate the detected predefined pattern, in addition to the plurality of indications of health events;
upon receiving a user selection specifying a first single point within the first graph structure, the first single point specifying a moment in time associated with the detected predefined pattern:
determining a third interval of time that is centered at the moment in time corresponding to the specified first single point, wherein the third interval of time is equal in duration to the second interval of time; and
updating the second graph structure by plotting a third plurality of values of the second biometric parameter on the second graph structure, with respect to the third interval of time; and
outputting the user interface for display using a display device.

2. The method of claim 1, wherein plotting the first plurality of values of the first biometric parameter on the first graph structure further comprises graphing values in the first plurality of values on an ordinal axis of the first graph structure as a function of time on an abscissa axis of the first graph structure.

3. The method of claim 1, wherein each of the plurality of indications of health events is inserted at a respective position on the first graph structure corresponding to a respective time at which the health event occurred, and wherein the determined positions are aligned parallel to an abscissa axis of the first graph structure and offset from the first plurality of values.

4. The method of claim 1, wherein each of the plurality of indications of health events is modified based on at least one of (i) a type of the respective indicated health event and (ii) a severity of the respective indicated health event, and wherein the modification comprises changing at least one of a color of the respective indication and a shape of the respective indication.

5. The method of claim 1, further comprising:
receiving a user selected duration of time for either the first graph structure or the second graph structure; and
updating the respective graph structure such that an abscissa axis of the respective graph structure spans the received duration.

6. The method of claim 1, further comprising:
receiving a request to display an adjacent interval of time, wherein the adjacent interval of time comprises an interval of time immediately preceding or subsequent to the first interval of time;
updating the first graph structure by plotting a fourth plurality of values of the first biometric parameter on the first graph structure that spans the adjacent interval of time; and
wherein the plurality of indications of health events are inserted at respective determined positions on the first graph structure, wherein the respective determined position for each of the plurality of indications of health events corresponds to a time at which each health event occurred, and wherein the determined positions are aligned parallel to an abscissa axis of the first graph structure and offset from the fourth plurality of values.

7. A non-transitory computer-readable storage medium storing code for execution by a processor, wherein the code, when executed by the processor, performs an operation for generating a user interface for monitoring biometric data collected by monitoring a user, the operation comprising:
generating a first portion of the user interface by plotting a first plurality of values of a first biometric parameter of a first type of biometric parameter on a first graph structure with respect to a first interval of time;
generating a second portion of the user interface by plotting a second plurality of values of a second biometric parameter of the first type of biometric parameter on a second graph structure with respect to a second interval of time that overlaps with only a portion of the first interval of time;
receiving a plurality of health events, the health events previously determined by classifying a second type of biometric parameter received by a monitoring device;
inserting a plurality of indications of the health events into the first graph structure;
detecting, using pattern recognition logic executing on a processor, a predefined pattern between the first plurality of values and the plurality of previously determined health events, wherein the first plurality of values is the first type of biometric parameter received by the monitoring device, and wherein the first type of biometric parameter is different from the second type of biometric parameter;

providing graphical feedback to indicate the detected predefined pattern, in addition to the plurality of indications of health events;

upon receiving a user selection specifying a first single point within the first graph structure, the first single point specifying a moment in time associated with the detected predefined pattern:

determining a third interval of time that is centered at the moment in time corresponding to the specified first single point, wherein the third interval of time is equal in duration to the second interval of time; and updating the second graph structure by plotting a third plurality of values of the second biometric parameter on the second graph structure, with respect to the third interval of time; and outputting the user interface for display using a display device.

8. The computer-readable storage medium of claim 7, wherein plotting the first plurality of values of the first biometric parameter on the first graph structure further comprises graphing values in the first plurality of values on an ordinal axis of the first graph structure as a function of time on an abscissa axis of the first graph structure.

9. The computer-readable storage medium of claim 7, wherein each of the plurality of indications of health events is inserted at a respective position on the first graph structure corresponding to a respective time at which the health event occurred, and wherein the determined positions are aligned parallel to an abscissa axis of the first graph structure and offset from the first plurality of values.

10. The computer-readable storage medium of claim 7, wherein each of the plurality of indications of health events is modified based on at least one of (i) the type of the respective indicated health event and (ii) the severity of the respective indicated health event, and wherein the modification comprises changing at least one of the color of the respective indication and the shape of the respective indication.

11. The computer-readable storage medium of claim 7, the operation further comprising:

receiving a user selected duration of time for either the first graph structure or the second graph structure; and updating the respective graph structure such that an abscissa axis of the respective graph structure spans the received duration.

12. The computer-readable storage medium of claim 7, the operation further comprising:

receiving a request to display an adjacent interval of time, wherein the adjacent interval of time comprises an interval of time equal in duration to the first interval of time and immediately preceding or subsequent to the first interval of time;

updating the first graph structure by plotting a fourth plurality of values of the first biometric parameter on the first graph structure that spans the adjacent interval of time; and wherein the plurality of indications of health events are inserted at respective determined positions on the first graph structure, wherein the respective determined position for each of the plurality of indications of health events corresponds to a time at which each health event occurred, and wherein the determined positions are aligned parallel to an abscissa axis of the first graph structure and offset from the fourth plurality of values.

13. A system comprising a memory containing a program that, when executed by a processor, performs an operation for generating a user interface for monitoring biometric data collected by monitoring a user, the operation comprising:

generating a first portion of the user interface by plotting a first plurality of values of a first biometric parameter of a first type of biometric parameter on a first graph structure with respect to a first interval of time;

generating a second portion of the user interface by plotting a second plurality of values of a second biometric parameter of the first type of biometric parameter on a second graph structure with respect to a second interval of time that overlaps with only a portion of the first interval of time;

receiving a plurality of health events, the health events previously determined by classifying a second type of biometric parameter received by a monitoring device;

inserting a plurality of indications of the health events into the first graph structure;

detecting, using pattern recognition logic executing on a processor, a predefined pattern between the first plurality of values and the plurality of previously determined health events, wherein the first plurality of values is the first type of biometric parameter received by the monitoring device, and wherein the first type of biometric parameter is different from the second type of biometric parameter;

providing graphical feedback to indicate the detected predefined pattern, in addition to the plurality of indications of health events;

upon receiving a user selection specifying a first single point within the first graph structure, the first single point specifying a moment in time associated with the detected predefined pattern:

determining a third interval of time that is centered at the moment in time corresponding to the specified first single point, wherein the third interval of time is equal in duration to the second interval of time; and updating the second graph structure by plotting a third plurality of values of the second biometric parameter on the second graph structure, with respect to the third interval of time; and outputting the user interface for display using a display device.

14. The system of claim 13, wherein plotting the first plurality of values of the first biometric parameter on the first graph structure further comprises graphing values in the first plurality of values on a first ordinal axis of the first graph structure as a function of time on a first abscissa axis of the first graph structure, wherein plotting the second plurality of values of the second biometric parameter on the second graph structure further comprises graphing values in the second plurality of values on a first ordinal axis of the second graph structure as a function of time on a first abscissa axis of the second graph structure, and wherein updating the second graph structure by plotting the third plurality of values of the second biometric parameter on the second graph structure comprises graphing values in the third plurality of values on an ordinal axis of the second graph structure as a function of time on an abscissa axis of the second graph structure.

15. The system of claim 13, wherein the plurality of indications of health events are inserted at respective determined positions on the first graph structure, wherein the respective determined position for each of the plurality of indications of health events corresponds to a time at which each health event occurred, and wherein the determined positions are aligned parallel to an abscissa axis of the first graph structure and offset from the first plurality of values; and modifying each of the plurality of indications of health events based on at least one of (i) a type of the respective indicated health event and (ii) a severity of the respective indicated health event, and wherein the modification comprises changing at least one of a color of the respective indication and a shape of the respective indication.

16. The system of claim 13, the operation further comprising:

receiving a user selected duration of time for either the first graph structure or the second graph structure; and updating the respective graph structure such that an abscissa axis of the respective graph structure spans the received duration.

17. The system of claim 13, the operation further comprising:

receiving a request to display an adjacent interval of time, wherein the adjacent interval of time comprises an interval of time equal in duration to the first interval of time and immediately preceding or subsequent to the first interval of time;

updating the first graph structure by plotting a fourth plurality of values of the first biometric parameter on the first graph structure that spans the adjacent interval of time; and wherein the plurality of indications of health events are inserted at respective determined positions on the first graph structure, wherein the respective determined position for each of the plurality of indications of health events corresponds to a time at which each health event occurred, and wherein the determined positions are aligned parallel to an abscissa axis of the first graph structure and offset from the fourth plurality of values.

18. The method of claim 1, further comprising:

receiving biometric data associated with a health event, wherein the biometric data was collected using a monitoring device and wherein the health event was classified as a first type of health event by the monitoring device based on biometric data received over a period of time;

determining a priority for the health event, based on the classified first type of the health event; and analyzing the data to reclassify the health event as a second type of health event, based on the determined priority for the health event, wherein an indication of the reclassified health event is inserted into the first graph structure.

19. The computer-readable storage medium of claim 7, the operation further comprising:

receiving biometric data associated with a health event, wherein the biometric data was collected using a monitoring device and wherein the health event was classified as a first type of health event by the monitoring device based on biometric data received over a period of time;

determining a priority for the health event, based on the classified first type of the health event; and analyzing the data to reclassify the health event as a second type of health event, based on the determined priority for the health event, wherein an indication of the reclassified health event is inserted into the first graph structure.

20. The system of claim 13, the operation further comprising:

receiving biometric data associated with a health event, wherein the biometric data was collected using a monitoring device and wherein the health event was classified as a first type of health event by the monitoring device based on biometric data received over a period of time;

determining a priority for the health event, based on the classified first type of the health event; and analyzing the data to reclassify the health event as a second type of health event, based on the determined priority for the health event, wherein an indication of the reclassified health event is inserted into the first graph structure.

* * * * *